United States Patent [19]

Golombek

[11] Patent Number: 5,001,068
[45] Date of Patent: Mar. 19, 1991

[54] METHOD FOR DETERMINING SOLIDIFICATION DEGREE OF CARRIER IMPREGNATED WITH REACTION RESIN

[75] Inventor: Joerg Golombek, Oberstenfeld, Fed. Rep. of Germany

[73] Assignee: Werzalit AG & CO, Oberstenfeld, Fed. Rep. of Germany

[21] Appl. No.: 206,869

[22] Filed: Jun. 9, 1988

[30] Foreign Application Priority Data

Jan. 19, 1988 [EP] European Pat. Off. ... EP88100652.2

[51] Int. Cl.$^5$ .......................................... G01N 33/44
[52] U.S. Cl. ........................................ 436/85; 73/64.1; 73/59
[58] Field of Search ..................... 436/85; 264/40.1; 73/54, 59, 64.1

[56] References Cited

U.S. PATENT DOCUMENTS

| 4,341,111 | 7/1982 | Husar | 73/64.1 |
| 4,535,621 | 8/1985 | Gervais et al. | 73/59 |
| 4,566,181 | 1/1986 | Matusik et al. | 73/59 |

FOREIGN PATENT DOCUMENTS

| 0259252 | 3/1988 | European Pat. Off. | 73/64.1 |
| 8805165 | 7/1988 | European Pat. Off. | 73/64.1 |

Primary Examiner—Robert J. Warden
Assistant Examiner—Laura E. Collins
Attorney, Agent, or Firm—Michael J. Striker

[57] ABSTRACT

For determining a solidification degree of a carrier impregnated with a reaction resin, a sample of the impregnated carrier is mounted on a holder, the sample is immersed into a fluid which is neutral relative to the carrier and has a temperature at which the reaction resin solidifies, the sample is moved in the fluid, and an energy required for moving the sample in the fluid is measured.

6 Claims, 2 Drawing Sheets

METHOD FOR DETERMINING SOLIDIFICATION DEGREE OF CARRIER IMPREGNATED WITH REACTION RESIN

BACKGROUND OF THE INVENTION

The present invention relates to a method of and an arrangement for determining a solidification degree of a carrier impregnated with a reaction resin, with the reaction resin solidifiable at a predetermined temperature.

Carriers impregnated with a reaction resin are known. They are formed, for example, as paper foils or fabric webs. Reaction resins which are solidified at a predetermined temperature include thermosetting plastics, for example aminoplastics, such as melamine resin, phenol resin or urea formaldehyde resin, or polyester and epoxy resin.

It is known to identify the condition of the reaction resin with A, B or C. A reaction resin in the condition A is liquid; it has short molecules. In the condition B the reaction resin no longer contains a solvent; a small part is condensed. In the condition C the molecules are unlimitedly long and they are irreversibly cross-linked with one another.

In the carrier impregnated with a reaction resin, the reaction resin is located in the condition B. Such impregnated carriers are further processed for different purposes, for example shaped bodies which are pre-pressed from a non-risable mixture of fibers and a heat hardenable binder are enveloped during a hot pressing at all sides with a protective and decorative layer composed of a carrier impregnated with a reaction resin.

Since the processability of the carriers impregnated with reaction resins depends on a plurality of parameters, such as the hardener fraction in the reaction resin and the properties of the carrier (pH value and moisture content), it is desirable to perform a measurement which would allow reliable and reproducable measuring results as to the properties of carriers impregnated with reaction resins.

SUMMARY OF THE INVENTION

Accordingly, it is an objective of the present invention to propose a method of and an arrangement for determining a solidification degree of a carrier impregnated with a reaction resin.

In keeping with these objectives and with others which will become apparent hereinafter, one feature of the present invention resides, briefly stated, in a method in accordance with which a sample of an impregnated carrier is mounted on a holder, which sample is immersed into a fluid which is neutral relative to the impregnated carrier and has a temperature at which the reaction resin hardens, the sample is moved in the fluid, and an energy required for the movement of the sample is determined.

From the measured values a diagram versus time is formed, which is typical for a carrier impregnated with predetermined reaction resin. Properties of the impregnated carrier can be clearly recognized on the thus formed diagram.

Another feature of the present invention is an arrangement which has means for mounting a sample of an impregnated carrier, means for accommodating a fluid which is neutral relative to the impregnated carrier and has a temperature at which the reaction resin hardens, so that the sample can be immersed into the fluid, means for moving the sample in the fluid, and means for measuring an energy required for the movement of the sample in the fluid. More particularly, the arrangement has a container which accommodates a test fluid, and a measuring head which is provided with a sample holder liftable and lowerable into the container and coupled with a reversible rotary drive, so that the sample holder with the sample is immersed into the test fluid in a lowered position of the measuring head.

In accordance with the method of the invention, the holder can be first rotated in a first rotary direction over a predetermined period of time, then maintained immovable over another predetermined period of time, and then rotated over a further predetermined period of time in a direction opposite to the direction of the first rotation.

A still further feature of the present invention is that the time of maintaining the holder in an immovable position is a multiple of the time of movement of the holder.

In accordance with another feature of the present invention, an electric current which is required for movement of the sample is measured.

Still another feature of the present invention is that during the movement of a sample a great number of current values is determined and from these values a measuring value is formed which is measured approximately after one-fourth, one-third at the beginning of the movement.

Finally, the sample can be reciprocably movable in the test fluid.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF A PREFERRED EMBODIMENT

Figure 1:
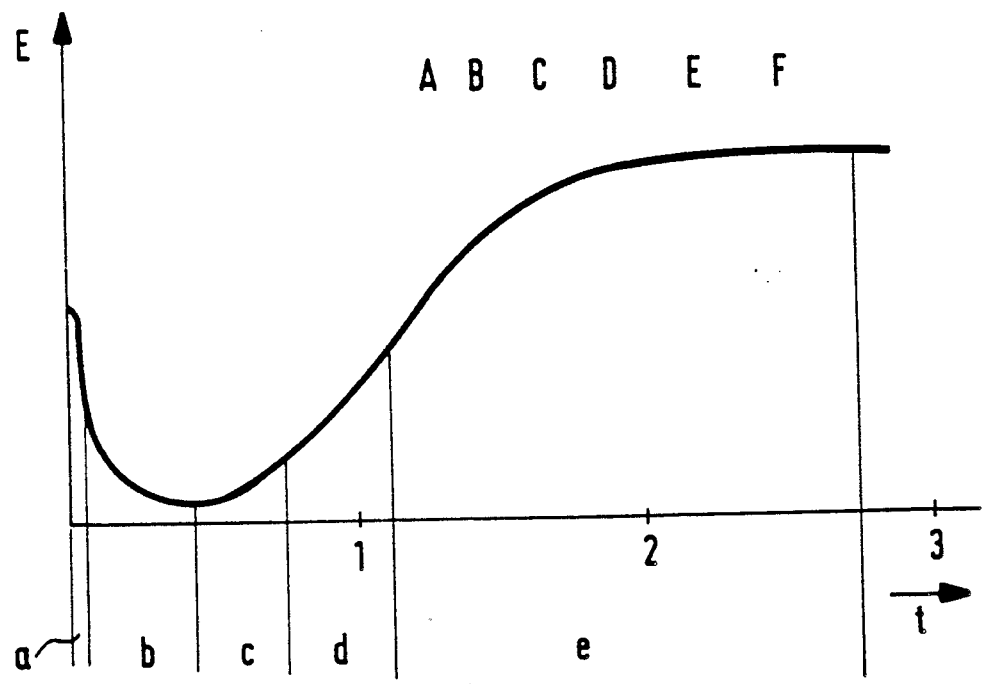
FIG. 1 is a view showing a diagram of solidification of a sample of carrier impregnated with reaction resins.

An arrangement for determination of a solidification degree of a carrier impregnated with a reaction resin has a container 1 for receiving a test fluid, as shown at the right side of this figure. When it is necessary to determine in the arrangement the data of a carrier which is impregnated with such a reaction resin which solidifies at a very high temperature, for example 200° C., then the container is provided with a heating and a device for maintaining a constant temperature of the test fluid. When the carrier is impregnated with a reaction resin which solidifies at low temperatures, the container is cooled and a device maintains a constant low temperature of the testing fluid. The cooling means, the heating means, and the devices for maintaining a constant temperature are well known and therefore they are not disclosed in detail.

A suitable testing fluid can be silicon oil which does not chemically react with the reaction resin and can be heated up to 200° C. A reversible rotation drive 3 is arranged above the container 1. The rotation drive is liftable and lowerable. Its drive shaft is coupled with a measuring head 4. The rotation drive must be controllable so that when it is turned on, the drive shaft of the rotation drive rotates either only in the same rotary direction, or its rotary direction can change from time to time. A sample holder 5 is mounted on the measuring head 4. A sheet-shaped impregnated support 6 is clamped perpendicularly on the sample support 5.

Figure 2:
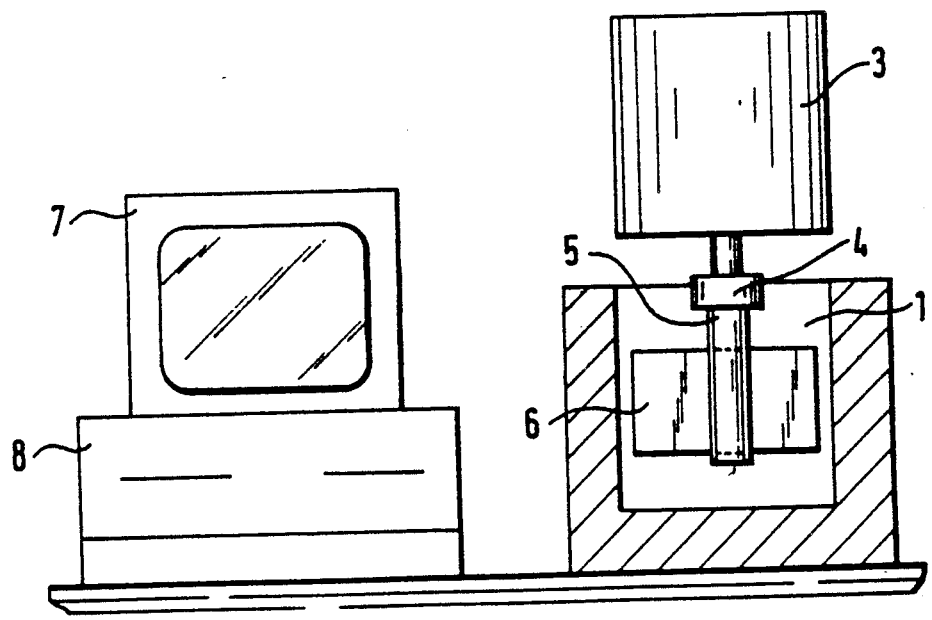
FIG. 2 is a view schematically showing an arrangement for determining a solidification degree of a carrier impregnated with a reaction resin.

Another part of the inventive arrangement is shown at the left side in FIG. 2. It has an image screen 7 and an electronic computer 8. This part is used for reproducing on the image screen a diagram of a sample with the desired properties, or in other words, an ideal diagram, if necessary as a still picture, and comparing the same with a diagram obtained from another sample.

FIG. 1 shows a typical course of such a diagram. As can be seen from this figure, the sample or in other words the carrier impregnated with a reaction resin has a predetermined rigidity at the time point $t=0$. The rigidity of the sample first sharply decreases, until it reaches its smallest very low value between b and c. At this time point the sample is in its softest state. Then the rigidity continuously increases until the diagram asymptotically reaches a maximum value. This means that from this time point which lies in FIG. 1 substantially at $t=3$, the rigidity of the sample no longer increases or in other words the reaction resin is solidified.

A row of parameters can be read from the diagram, which parameters are important for processing of the impregnated carrier. The region a of the diagram has no influence on the later processability of the impregnated carrier. The regions b and c of the diagram are representative for the flow condition of the reaction resin. In accordance with the course of the diagram in this region it can be recognized whether the impregnated carrier becomes unusable as a result of long storage.

In the region d the steepness of the diagram is for example representative of a value of the hardener concentration in the reaction resin. In the region e the different hardening degrees A to F are represented in the diagram. A corresponds to the time point at which the reaction resin in the impregnated carrier is almost completely hardened, which for individual cases of application is desirable or sufficient.

The diagram shown in FIG. 1 is produced in such a manner, that the electrical current which is required for the movement of the sample in the test fluid is measured from the time point of the dipping of the sample into the test fluid to the complete hardening of the reaction resin. For producing the diagram shown in FIG. 1, the sample dipped in the testing fluid is rotated in one rotary direction, for example during 1 second. Then the sample is not moved during 3 seconds, and finally it is rotated in an opposite rotary direction for 1 second.

Figure 3:
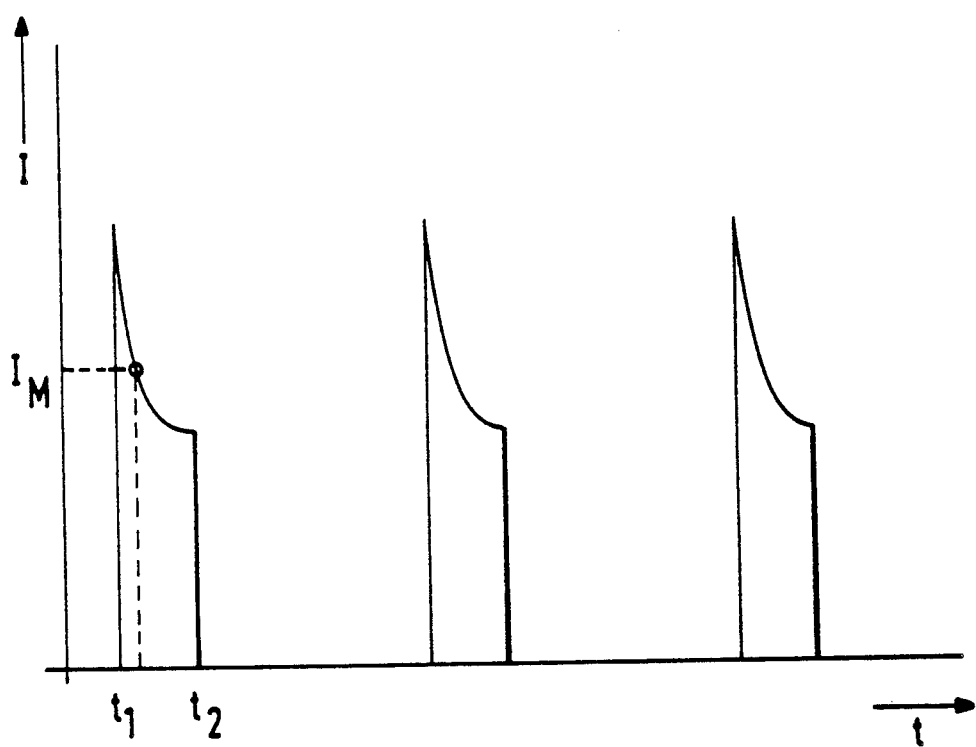
FIG. 3 is a view showing a course of a motor current in dependence upon time when a holder of the inventive arrangement moves with a sample of the impregnated carrier in the fluid.

The current I which is required for movement of the sample is shown versus time t in FIG. 3 for three successive movement steps. As can be seen from FIG. 3, at the beginning of each movement which continues for example from $t_1$ to $t_2$, a relatively high current is needed. It must cause on the one hand the switching-on current of the motor and, to accelerate the mass of the sample and the testing fluid surrounding the sample on the other hand. The value of this current is not representative for energy which is required for overcoming the rigidity of the sample. The longer the movement continues, the stronger decreases the current in accordance with FIG. 3. The value of current at the time point $t_2$ is really not representative for the energy which is required for overcoming of the rigidity of the sample. The closer is the movement to the time $t_2$, the stronger acts the kinetic energy on the sample, which is produced by the acceleration of the sample and the testing fluid which surrounds the latter.

For making the diagram which is shown in FIG. 1, the current value $I_M$ is formed which corresponds to the current at a time point where substantially one-fourth to one-third of the switching period is elapsed.

In the practice the current measurement is performed so that in the time period between $t_1$ and $t_2$ automatically approximately 300 measurements are made and a measured current value of a predetermined delaying time period after $t_1$ is taken for the diagram in accordance with FIG. 1. The delaying time interval can be determined experimentally. It depends on the properties of the arrangement, such as the type of the used motor, the viscosity of the test fluid, and the dimension of the sample.

For many practical applications the current measurement produces sufficiently accurate values for the energy which is required for movement of the sample. When, however, more accurate values are needed, it is also possible to make a torque measurement. This measurement can be performed with known means; however, it involves a higher apparatus expense.

The present invention is described hereinabove in such embodiment, in accordance with which the sample performs a rotary movement. It is to be understood that it is also possible to implement the inventive idea with a sample which performs a linear movement in the testing fluid, for example a swinging or pendular movement.

The inventive method and arrangement are useful in many cases for processing of carriers impregnated with reaction resins, for example, from the product receiving testing of the supplied impregnated carriers to the determination of the processing parameters.

It will be understood that each of the elements described above, or two or more together, may also find a useful application in other types of constructions differing from the types described above.

While the invention has been illustrated and described as embodied in an arrangement and a method for testing a hardening degree of a carrier impregnated with a reaction resin, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of determining a solidification degree of a carrier impregnated with a reaction resin solidifiable at a predetermined temperature, the method comprising mounting a probe of an impregnated carrier on a holder; immersing the probe into a fluid which is neutral relative to the impregnated carrier and has a temperature at which the reaction resin is solidified; moving the probe in the fluid; and measuring an energy which is required for performing the movement wherein said energy measurement is an indication as to the degree of solidification.

2. A method as defined in claim 1, wherein said step of moving the probe in the fluid includes first rotating the holder during a predetermined period of time in one direction; maintaining the holder immovable during a predetermined period of time; and then rotating the holder during a predetermined period of time in a direction of rotation which is opposite to said first mentioned direction of rotation.

3. A method as defined in claim 2, wherein said maintaining the holder immovable includes maintaining the holder immovable during a predetermined period of time which is a multiple of the period of time of rotating the holder in any of said directions.

4. A method as defined in claim 1, wherein said moving includes supplying an electric current for the moving of the sample, said measuring includes measuring the electric current supplied for moving the sample.

5. A method as defined in claim 4, wherein said step of determining the electric current includes determining during the periods of time of moving the sample a plurality of current values and forming from these values a measuring value which was measured approximately after one-fourth to one-third after a beginning of the period of time of moving the sample.

6. A method as defined in claim 1, wherein said moving step includes reciprocating the sample in the fluid.

* * * * *